United States Patent
Kimless et al.

(10) Patent No.: US 11,951,086 B2
(45) Date of Patent: Apr. 9, 2024

(54) TABLET OR COMPOSITION HAVING N-ACYL ETHANOLAMINE AND CANNABINOID

(71) Applicant: PURE GREEN PHARMACEUTICALS, INC., West Bloomfield, MI (US)

(72) Inventors: Debra Kimless, Chadds Ford, PA (US); John S. Althaus, Saline, MI (US); Stephen Goldner, West Bloomfield, MI (US)

(73) Assignee: PURE GREEN PHARMACEUTICALS, INC., West Bloomfield, MI (US)

( * ) Notice: Subject to any disclaimer, the term of this patent is extended or adjusted under 35 U.S.C. 154(b) by 359 days.

(21) Appl. No.: 17/044,521

(22) PCT Filed: Apr. 3, 2019

(86) PCT No.: PCT/US2019/025476
§ 371 (c)(1),
(2) Date: Oct. 1, 2020

(87) PCT Pub. No.: WO2019/195355
PCT Pub. Date: Oct. 10, 2019

(65) Prior Publication Data
US 2021/0015774 A1    Jan. 21, 2021

Related U.S. Application Data

(60) Provisional application No. 62/651,775, filed on Apr. 3, 2018.

(51) Int. Cl.
*A61K 31/192* (2006.01)
*A61K 9/107* (2006.01)
(Continued)

(52) U.S. Cl.
CPC .......... *A61K 31/192* (2013.01); *A61K 9/107* (2013.01); *A61K 9/20* (2013.01); *A61K 31/01* (2013.01); *A61K 31/16* (2013.01); *A61P 29/02* (2018.01)

(58) Field of Classification Search
CPC .............................. A61K 31/192; A61K 9/107
See application file for complete search history.

(56) References Cited

U.S. PATENT DOCUMENTS 9,044,390 B1 *  6/2015  Speier ................... A61K 36/00
2016/0039591 A1  2/2016  Kinzer
(Continued)

FOREIGN PATENT DOCUMENTS

WO    2015068052    5/2015
WO    2016174661    11/2016

OTHER PUBLICATIONS

Gabrielsson, L., Mattsson, S., and Fowler, C.J. (2016). Palmitoylethanolamide for the treatment of pain: Pharmacokinetics, safety and efficacy. British Journal of Clinical Pharmacology. vol. 82. pp. 932-942.
(Continued)

*Primary Examiner* — Svetlana M Ivanova
(74) *Attorney, Agent, or Firm* — Carlson, Gaskey & Olds, P.C.

(57) ABSTRACT

A composition includes n-acyl ethanolamine, at least one cannabinoid, and at least one terpene. The composition may be in the form of a tablet.

18 Claims, 3 Drawing Sheets

(51) Int. Cl.
*A61K 9/20* (2006.01)
*A61K 31/01* (2006.01)
*A61K 31/16* (2006.01)
*A61P 29/02* (2006.01)

(56) References Cited

U.S. PATENT DOCUMENTS

2017/0252300 A1* 9/2017 Modi .................... A61K 9/0053
2018/0064645 A1* 3/2018 Greenspoon ......... A61K 31/352
2018/0078523 A1* 3/2018 Shmulewitz ......... A61K 31/352
2021/0052478 A1* 2/2021 Yardley ................. A61K 47/06

OTHER PUBLICATIONS

European Search Report for European Patent Application No. 19781930.3 dated Dec. 1, 2021.
International Preliminary Report on Patentability for International Application No. PCT/US2019/025476 dated Oct. 15, 2020.
International Search Report and Written Opinion for International Application No. PCT/US2019/025476 completed Jun. 20, 2019.

* cited by examiner

TABLET OR COMPOSITION HAVING N-ACYL ETHANOLAMINE AND CANNABINOID

CROSS-REFERENCE TO RELATED APPLICATIONS

This disclosure claims priority to U.S. Provisional Patent Application No. 62/651,775 filed on Apr. 3, 2018.

BACKGROUND

Cannabis is used for medicinal reasons to treat disease or alleviate symptoms. For example, the active chemicals in medicinal cannabis can be delivered into the body through inhalation, ingestion, or topical application. Delivery of medicinal cannabis through mucosal membranes is of particular interest due to rapidity of uptake without the detrimental effects associated with inhalation.

SUMMARY

A composition according to an example of the present disclosure includes n-acyl ethanolamine, at least one cannabinoid, and at least one terpene.

In a further embodiment of any of the foregoing embodiments, the n-acyl ethanolamine is selected from the group consisting of olioylethanolamide, palmitoylethanolamide, and combinations thereof.

In a further embodiment of any of the foregoing embodiments, the n-acyl ethanolamine is palmitoylethanolamide.

In a further embodiment of any of the foregoing embodiments, the at least one cannabinoid includes cannabigerolic acid.

In a further embodiment of any of the foregoing embodiments, the at least one terpene is selected from the group consisting of myrcene, limonene, caryophyllene, linalool, pinene, and combinations thereof.

In a further embodiment of any of the foregoing embodiments, the n-acyl ethanolamine is palmitoylethanolamide. The at least one cannabinoid includes cannabigerolic acid, and the at least one terpene includes myrcene.

In a further embodiment of any of the foregoing embodiments, including by weight, 1 to 2000 parts of the n-acyl ethanolamine and 1 to 2000 parts of the at least one cannabinoid.

In a further embodiment of any of the foregoing embodiments, including by weight, 10 to 1800 parts of the n-acyl ethanolamine and 1 to 100 parts of the at least one cannabinoid.

In a further embodiment of any of the foregoing embodiments, the n-acyl ethanolamine is in the form of micelles that facilitate transmucosal migration of the cannabinoid across mucosa and capillary blood vessels into bloodstreams in mammals.

In a further embodiment of any of the foregoing embodiments, the n-acyl ethanolamine is in the form of micelles, and the at least one cannabinoid is entrapped in the micelles.

In a further embodiment of any of the foregoing embodiments, clinical activities associated with the administration of a sublingual tablet of the composition include: chronic and neuropathic pain, inflammation, including peripheral neuropathies such as diabetic neuropathy, chemotherapy induced peripheral neuropathy, carpal tunnel syndrome, phantom limb pain, sciatic pain, osteoarthritis, low back pain, musculo-skeletal pain, failed back surgery syndrome, fibromyalgia, dental pain, post-stroke neuropathic pain, pain from multiple sclerosis, chronic pelvic pain, intestinal inflammation, migraine, cerebral ischemia, complex regional pain syndrome, postherpetic neuralgia, chronic pain from Lyme's Disease, ALS, urinary pain, and vaginal pain.

A tablet according to an example of the present disclosure includes one or more excipients, n-acyl ethanolamine, at least one cannabinoid, and at least one terpene.

In a further embodiment of any of the foregoing embodiments, the n-acyl ethanolamine is selected from the group consisting of olioylethanolamide, palmitoylethanolamide, and combinations thereof.

In a further embodiment of any of the foregoing embodiments, the at least one cannabinoid includes cannabigerolic acid.

In a further embodiment of any of the foregoing embodiments, the at least one terpene is selected from the group consisting of myrcene, limonene, caryophyllene, linalool, pinene, and combinations thereof.

In a further embodiment of any of the foregoing embodiments, the n-acyl ethanolamine is palmitoylethanolamide. The at least one cannabinoid includes cannabigerolic acid, and the at least one terpene includes myrcene.

In a further embodiment of any of the foregoing embodiments, including by weight, 10 to 1800 parts of the n-acyl ethanolamine and 1 to 100 parts of the at least one cannabinoid.

In a further embodiment of any of the foregoing embodiments, the n-acyl ethanolamine is in the form of micelles, and the at least one cannabinoid is entrapped in the micelles.

A sublingual tablet according to an example of the present disclosure includes a compressed powder containing one or more excipients, at least one cannabinoid, at least one terpene, and a transmucosal carrier capable of binding with the at least one cannabinoid for transmucosal migration.

In a further embodiment of any of the foregoing embodiments, the transmucosal carrier is in the form of non-oriented molecules.

In a further embodiment of any of the foregoing embodiments, the transmucosal carrier is in the form of micelles, and the at least one cannabinoid is entrapped in the micelles.

In a further embodiment of any of the foregoing embodiments, the transmucosal carrier is selected from the group consisting of olioylethanolamide, palmitoylethanolamide, and combinations thereof.

In a further embodiment of any of the foregoing embodiments, the transmucosal carrier is palmitoylethanolamide. The at least one cannabinoid includes cannabigerolic acid, and the at least one terpene includes myrcene.

In a further embodiment of any of the foregoing embodiments, the transmucosal carrier is in the form of micelles that facilitate transmucosal migration of the at least one cannabinoid across mucosa and capillary blood vessels into bloodstreams in mammals.

In a further embodiment of any of the foregoing embodiments, clinical activities associated with the administration of the sublingual tablet include: chronic and neuropathic pain, inflammation, including peripheral neuropathies such as diabetic neuropathy, chemotherapy induced peripheral neuropathy, carpal tunnel syndrome, phantom limb pain, sciatic pain, osteoarthritis, low back pain, musculo-skeletal pain, failed back surgery syndrome, fibromyalgia, dental pain, post-stroke neuropathic pain, pain from multiple sclerosis, chronic pelvic pain, intestinal inflammation, migraine, cerebral ischemia, complex regional pain syndrome, postherpetic neuralgia, chronic pain from Lyme's Disease, ALS, urinary pain, and vaginal pain.

BRIEF DESCRIPTION OF THE DRAWINGS

The various features and advantages of the present disclosure will become apparent to those skilled in the art from the following detailed description. The drawings that accompany the detailed description can be briefly described as follows.

DETAILED DESCRIPTION

The therapeutic benefit of small molecules originating from cannabis results from the activation of the endocannabinoid system and other non-endocannabinoid receptors and ion channels. The endocannabinoid system includes an extensive array of receptors (CB1 and CB2) and channels (TRP) throughout the peripheral and central nervous system. Interaction of cannabinoids and their entouragic participants (e.g., terpenes and fatty acid ethanolamides) work together by affecting a homeostatic balance in neurotransmission resulting in therapeutic benefit such as pain relief in particular. The invention operates within this therapeutic realm.

Figure 1:
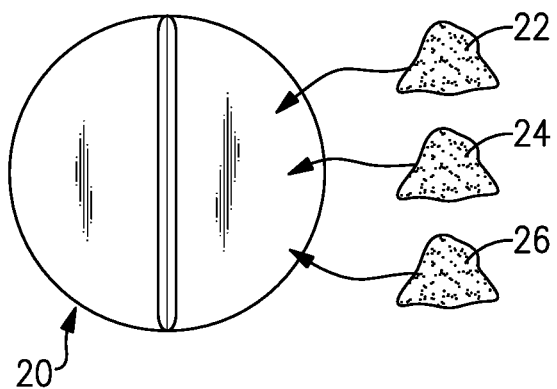
FIG. 1 illustrates an example tablet formed of the disclosed composition.

FIG. 1 schematically illustrates an example tablet 20 for sublingual administration to provide pain relief in humans and other mammals. The tablet 20 is a compressed mixture of one or more powders. It is to be appreciated that the tablet 20 is presented herein to demonstrate a non-limiting example of a composition, which will be described in more detail below, and that the composition may be adapted for other forms of therapeutic administration.

In particular, sublingual delivery effectiveness depends on the ability of the chemicals being delivered to migrate through the mucosa and capillary blood vessel into the bloodstream. This poses challenges for sublingual delivery of cannabis-based chemicals, which are typically in the form of oils that are practically insoluble in water and have poor migration—and thus poor sublingual delivery effectiveness. In this regard, as will be appreciated from the present disclosure, the disclosed composition is clinically active in the cannabinoid system of mammals to enhance sublingual migration of cannabis-based chemicals to produce medical benefits in lowering pain.

The composition of the tablet 20 includes n-acyl ethanolamine 22, at least one cannabinoid 24, and at least one terpene 26. Of these ingredients, the cannabinoid and the n-acyl ethanolamine are active ingredients in the cannabinoid system of mammals, while the terpene is considered to be an inactive ingredient. Depending on the form for medicinal administration of the composition, other inactive ingredients may also be used with the above composition. In the example of the tablet 20, the composition may additionally include excipients or other inactive ingredients. Excipients may be selected to provide desired characteristic release of the active ingredients. As an example, the excipient or excipients may be selected for fast release in the case of sublingual administration. Excipients for this purpose may include mannitol, polyvinyl alcohol, polyvinypyrrolidone and stearate, but the excipients in general are not limited and may additionally or alternatively include fillers, binders, disintegrants, and lubricants.

In examples, the n-acyl ethanolamine is palmitoylethanolamide (PEA), olioylethanolamide (OEA), or a combination thereof. In further examples, the cannabinoid 24 is or includes cannabigerolic acid (CBGA). CBGA is a precursor molecule of other cannabinoids, such as tetrahydrocannabinol (delta-g-tetrahydrocannabinol or delta-8-tetrahydrocannabinol, commonly known as "THC") and cannabidiol (CBD). Cannabinoids may include, but are not limited to, THC, CBD, cannabinol, cannabavarin, cannabigerol, cannabichromene, cannabicyclol, cannabitriol, cannabielsoin, and non-endogenous cannabinoids. In further examples, the terpene or terpenes can include, but are not limited to, myrcene, limonene, caryophyllene, linalool, and pinene.

The amounts of the ingredients in the tablet 20 and composition, and in particular the active ingredients, can be selected within pharmaceutically-effective amounts per dose. For example, pharmaceutically-effective amounts are those amounts that clinically reduce pain in mammals. As will be appreciated, due to the enhanced effectiveness of sublingual bioavailability of the disclosed composition, such amounts may differ from effective amounts known for other cannabinoid-containing compositions. In particular, the pharmaceutically-effective amounts of the disclosed composition will be less than effective amounts known for other cannabinoid-containing compositions. Alternatively, it is also contemplated that for equivalent amounts of the disclosed composition to other cannabinoid-containing compositions, the disclosed composition will produce a greater therapeutic effect in reduction of pain due to the enhanced sublingual bioavailability.

In general, however, the disclosed composition can include, by weight, 1 to 2000 parts of the n-acyl ethanolamine and 1 to 2000 parts of the cannabinoid or combined amount of cannabinoids. As an example, the unitary part by weight is 1 milligram. In further examples, the composition includes 10 to 1800 parts of the n-acyl ethanolamine and 1 to 100 parts of the cannabinoid or combined amount of cannabinoids. In one example, a tablet includes 10 milligrams of CBD, 100 milligrams of PEA, and 0.1 milligrams of terpenes (myrcene, linalool, B caryophylline, and humulene).

Figure 2:
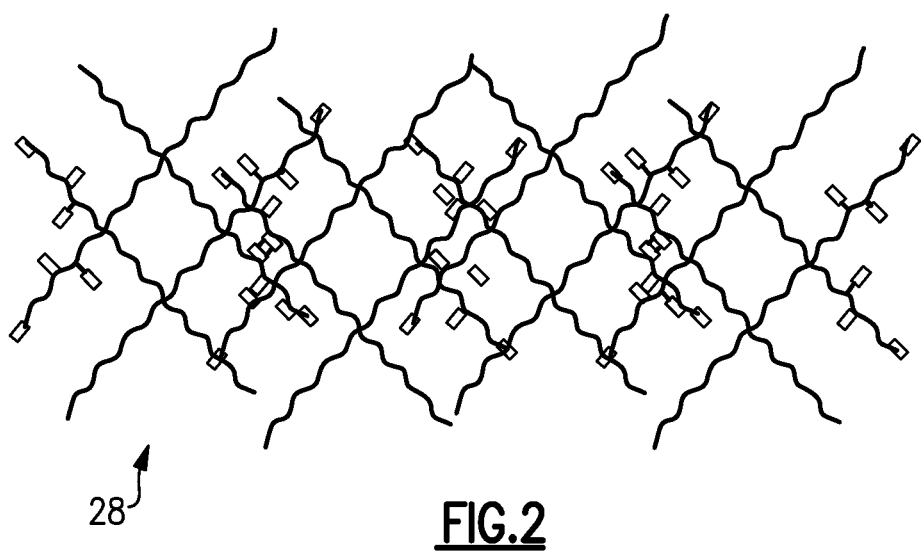
FIG. 2 illustrates a non-oriented form of palmitoylethanolamide.

The n-acyl ethanolamine, for example the PEA, can exist in at least two structural configurations, either of which or both of which can be used in the composition. One of these configurations is in the form of non-oriented molecules, an example of which is shown at 28 in FIG. 2. The other of these configurations is in the form of micelles, an example of which is shown at 30 in FIG. 3.

The n-acyl ethanolamine or PEA is generally insoluble in water. However, when placed in an aqueous environment, the n-acyl ethanolamine or PEA molecules self-assemble into micelles. A micelle is an aggregate of molecules that is usually spherical. In the aggregate, the hydrophilic heads of the molecules face outwards from the center of the sphere, while the hydrophobic tails face inwards toward the center of the micelle. For PEA, the hydrophilic heads comprise the alcohol moieties and the hydrophobic tails comprise the fatty acid moieties. In the micelle form, the PEA is water soluble.

In one example, the disclosed composition includes the n-acyl ethanolamine or PEA in the form of the non-oriented molecules. In this case, when the n-acyl ethanolamine or PEA is exposed to an aqueous environment, such as sublingual saliva, the n-acyl ethanolamine or PEA activates to self-assemble into the micelles. That is, the n-acyl ethanolamine or PEA seeks to achieve a lower energy state in situ.

Additionally or alternatively, the composition includes, prior to therapeutic administration, the n-acyl ethanolamine or PEA preassembled in the micelle form. For example, prior to incorporation into the composition, the n-acyl ethanolamine or PEA is mixed into an aqueous solution and optionally agitated. The concentration of the solution may be varied but in one non-limiting example, the aqueous solution may have a concentration of approximately 10 g/L of the n-acyl ethanolamine or PEA in water. The agitation may include sonication. For example, the resulting product is an aqueous n-acyl ethanolamine or PEA emulsion in which particle size may range from about 0.1 micrometers to 1 micrometer. The emulsion can then be filtered and the filtrate then lyophilized to yield a powder containing dry n-acyl ethanolamine or PEA micelles. The dry n-acyl ethanolamine or PEA micelles can then be incorporated into the composition. In this example, the n-acyl ethanolamine or PEA would be released into the saliva in a form that is already water soluble, which may facilitate increasing the rate of delivery. That is, the self-assembly step of forming the micelle as with the non-oriented molecules is eliminated by using preassembled n-acyl ethanolamine or PEA micelles.

Figure 3:
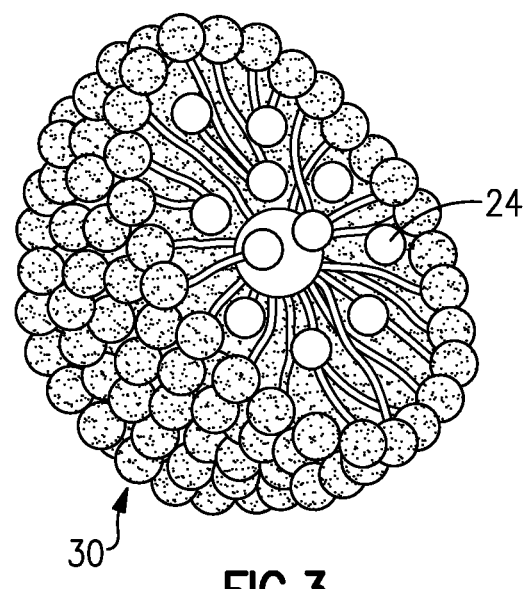
FIG. 3 illustrates a micelle structure of palmitoylethanolamide.

The micelles also facilitate transmucosal migration of the cannabinoid. For example, the n-acyl ethanolamine or PEA in the non-oriented molecule form can be exposed to an aqueous environment that also includes the cannabinoid 24. The micelles thus assemble in the presence of the cannabinoid 24 and, as also shown in FIG. 3, the cannabinoid 24 thereby becomes incorporated into the micelle 30. In this regard, the n-acyl ethanolamine or PEA serves as a carrier of the cannabinoid 24.

The n-acyl ethanolamine or PEA is bound with the cannabinoid 24. The binding between the n-acyl ethanolamine or PEA and the cannabinoid 24 is not chemical bonding in the sense of ionic or covalent bonding. Rather, the aggregate of the n-acyl ethanolamine or PEA molecules in the micelle structure physically entraps the cannabinoid 24 molecules, although there may be secondary bonding. In this case, the cannabinoid 24 is hydrophobic and is "packaged" in the hydrophobic interior pocket of the micelle. This occurs spontaneously at standard temperature and pressure via self-assembly by thermodynamic considerations. If preassembled micelle are used in the composition, such entrapment may be conducted prior to therapeutic administration, during the preassembly of the n-acyl ethanolamine or PEA into the micelle form by adding the cannabinoid 24 to the mixture. If the non-oriented n-acyl ethanolamine or PEA is used in the composition, the entrapment may occur in vivo in the saliva during administration. As an example based on preassembled micelle, 100 mg of PEA may be included in a tablet. The 100 mg of PEA is preassembled into the micelle in the presence of 10 mg of THC prior to formation of the tablet. The 10 mg of THC incorporates into the 100 mg of PET micelles. The final tablet thus contains 10 mg of THC per 100 mg of PEA micelle as a lyophilized powder, which may be a component of a 250 mg tablet.

Depending on the concentration of the n-acyl ethanolamine or PEA in an aqueous environment, the equilibrium between the non-oriented molecule form and the micelle form may favor the insoluble non-oriented molecule form. However, in vivo, as the concentration of the micelles are depleted by removal from an aqueous matrix (e.g. saliva) through tissue absorption, the equilibrium may favor conversion of the insoluble form. Thus, over time, the insoluble form will also deplete in the absence of other mechanisms (metabolism).

The therapeutic administration of the tablet 20 or composition may include placement into a sublingual space of a mammal. This results in dissolution of the composition into the sublingual space. During dissolution the active ingredients are released from the tablet 20 or composition. If the n-acyl ethanolamine or PEA is in the non-oriented molecule form, the n-acyl ethanolamine or PEA self-assembles into the micelle structure upon release. If the n-acyl ethanolamine or PEA are provided preassembled in micelles, the micelles are released intact into the saliva.

Figure 4:
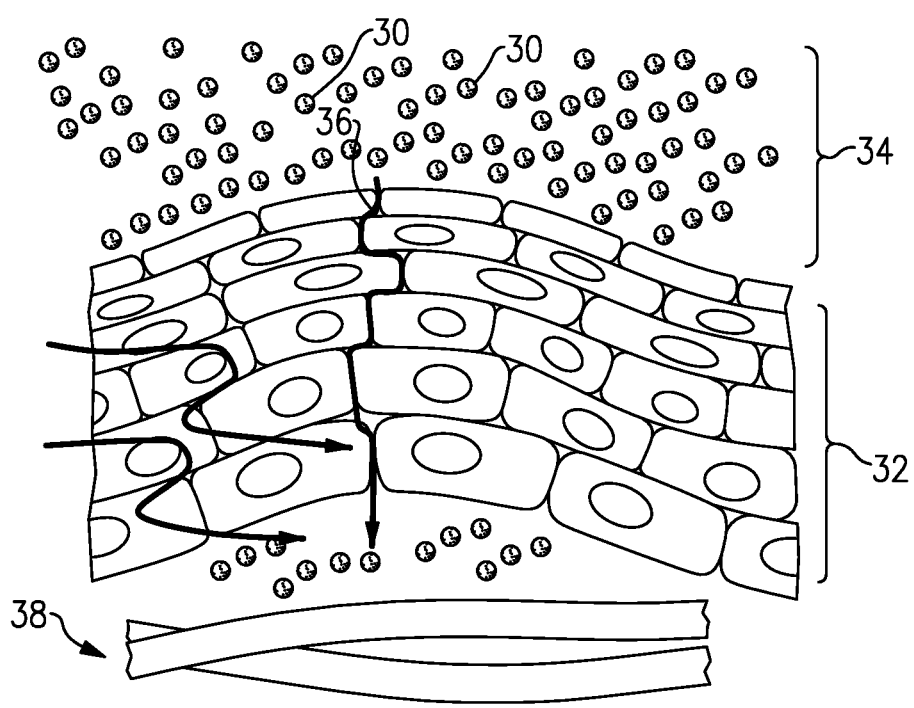
FIG. 4 illustrates transmigration of micelle across a mucosa.
Figure 5:
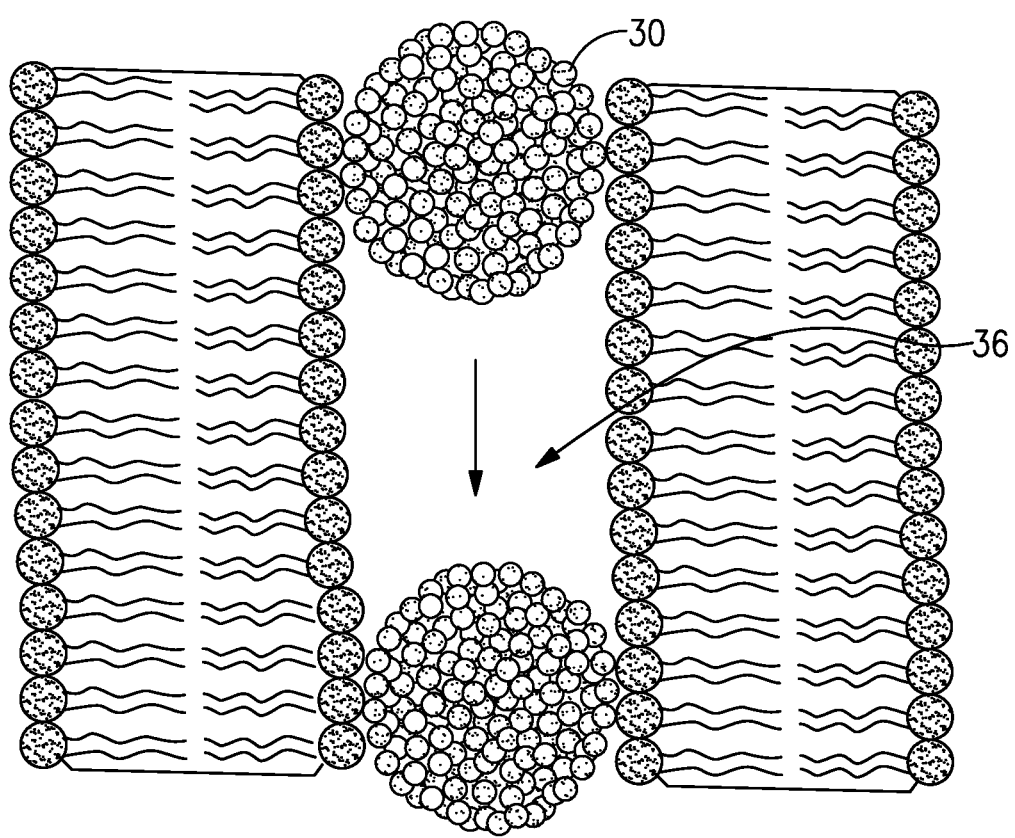
FIG. 5 illustrates a magnified view of transmigration of micelle along an intra-mucosal pathway.

FIG. 4 illustrates an example of transmigration of the micelles 30 (which may include the cannabinoid 24) across a mucosa 32. The micelle 30 begin in an extra-mucosa space 34 and transmigrate along an intra-mucosa pathway 36 through tight junctions of the mucosa cell lining toward a capillary bed 38. FIG. 5 illustrates the transmigration of the micelles 30 along the intra-mucosa pathway 36 between lipid bilayers of mucosa cells. Transmigration is facilitated by the flexibility of the micelle 30, which can change shape to accommodate variation the topography of the pathway 36. The transmigration is facilitated by the polar head groups of the micelle, which interact with the polar head groups of the lipid bilayer of cells. In this manner, the n-acyl ethanolamine or PEA, especially in micelle form, facilitates the water solubility and transport of the cannabinoid 24 across the mucosa. In this manner cannabis delivery to the bloodstream in mammals is facilitated by micellar PEA when administered sublingually. A synergistic affect is thereby realized at reduced concentrations.

Study

A clinical trial was conducted using an example of the disclosed composition for 16 patients ranging in age from 20 to 87, both male and female. Pain scale scores ranged from a 3-8 prior to taking our tablets. Inclusion criteria were mild to moderate pain that was not currently being treated, to avoid overlap of medications. Any patient taking concomitant pain medication were disqualified from the trial. Tablet composition included: 10 mg CBD, 100 mg PEA, 0.1 mg terpenes: myrcene, linalool, B caryophylline, and humulene.

Patients were provided with instructions and a diary. They were instructed to assess and document their pain on a pain scale score of 0-10 using VAS (visual analog scale) and Wong-Baker Faces Pain Rating Scale to help with the VAS scoring:

1. At the onset of pain, initially take one-half of a tablet and place it under your tongue. The tablet will dissolve rapidly in about 60 seconds or less. The patient may swallow normally, but do not eat or drink anything for 3-5 minutes post dose.
2. Record the date, time, dose, and initial pain score using the patient diary form.
3. After 20 minutes, note the pain score and record in the patient diary.
4. Repeat the pain assessment and record score at 40, 60, and 120 minutes.
5. If after 20 minutes, there is not pain relief or not completely relieved, take the second ½ tablet and repeat instructions in Step 1.
6. If the pain is persistent, you may continue to dose, as needed, but not to exceed 3 whole tablets in a 24 hour period. If additional dosing is required, follow the sequence of steps above and record in the patient diary. Measurement parameters: VAS scores, patient reports of pre and post treatment pain. Patients were encouraged to take notes to describe pre and post treatment pain and how it would compare with their usual treatment.

Outcomes:
Patient 1: Female, 56 chronic neuropathic pain
Time: 0 20 40 60 120
PSS: 6 2 2 1 1
Patient 2: Female 63, acute low back pain
Time: 0 20 40 60 120
PSS: 4 3 (½ tab) 0 0 0
Patient 3: Male 87 chronic 5 feet, knees, pain
Time: 0 20 40 60 120
PSS: 6 4 3 2 0
Patient 4: Male 32 low back pain
Time: 0 20 40 60 120
PSS: 52000
Patient 5: Female 42 low back and hip pain
Time: 0 20 40 60 120
PSS: 6 3 3 (½ tab) 1 1
Patient 6: Male. 32 chronic leg/knee pain
Time: 0 20 40 60 120
PSS: 5 2 2 (½ tablet) 0 0
Patient 7: Male 57 chronic foot pain
Time: 0 20 40 60 120
PSS: 60000
Patient 8: Female 23 dysmenorrhea
Time: 0 20 40 60 120
PSS 31000
Patient 9: Female 5 25 low back pain
Time: 0 20 40 60 120
PSS: 6 2 2 (½ tab) 0 0
Patient 10: Male 48 chronic low back pain, shoulder pain
Time: 0 20 40 60 120
PSS: 6 3 3 (½ tab) 0 0
Patient 11: Female 63 headache (hangover)
Time: 0 20 40 60 120
PSS 4 2 (½ tab) 0 0 0
Patient 12: Male 48, tooth pain after tooth surgery
Time: 0 20 40 60 120
PSS: 8 5 4 (½ tab) 2 2
Patient 13: Female 56 Shoulder pain
Time: 0 20 40 60 120
PSS: 6 1 0 00
Patient 14: Female 56 headache, low back pain
Time: 0 20 40 60 120
PSS: 4 0 0 0 0
Patient 15: Female 20 headache
Time: 0 20 40 60 120
PSS: 3 0 0 0 0
Patient 16: Female 63 Fibromyalgia, neck, upper back pain
Time: 0 20 40 60 120
PSS: 4 2 (½ tab) 1 1 0
Study Summary:
Average age 53.2
10 females
6 males
Average starting VAS score=5.1
Average pain score 20 mins=2.0
Average pain score 40 mins=1.25
Average pain score 60 mins=0.43
Average pain score 120 mins=0.25

In summary, indications include but are not limited to: chronic and neuropathic pain and inflammation, including peripheral neuropathies such as diabetic neuropathy, chemotherapy induced peripheral neuropathy, carpal tunnel syndrome, phantom limb pain, sciatic pain, osteoarthritis, low back pain, musculo-skeletal pain, failed back surgery syndrome, fibromyalgia, dental pain, post-stroke neuropathic pain, pain from multiple sclerosis, chronic pelvic pain, intestinal inflammation, migraine, cerebral ischemia, complex regional pain syndrome, postherpetic neuralgia, chronic pain from Lyme's Disease, ALS, urinary pain, and vaginal pain and is neuroprotective.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A composition comprising:
   n-acyl ethanolamine;
   at least one cannabinoid; and
   at least one terpene, wherein the n-acyl ethanolamine is in the form of lyophilized, dry preassembled micelles, and the at least one cannabinoid is entrapped in the micelles.

2. The composition as recited in claim 1, wherein the n-acyl ethanolamine is selected from the group consisting of olioylethanolamide, palmitoylethanolamide, and combinations thereof.

3. The composition as recited in claim 1, wherein the n-acyl ethanolamine is palmitoylethanolamide.

4. The composition as recited in claim 1, wherein the at least one cannabinoid includes cannabigerolic acid.

5. The composition as recited in claim 1, wherein the at least one terpene is selected from the group consisting of myrcene, limonene, caryophyllene, linalool, pinene, and combinations thereof.

6. The composition as recited in claim 1, wherein the n-acyl ethanolamine is palmitoylethanolamide, the at least one cannabinoid includes cannabigerolic acid, and the at least one terpene includes myrcene.

7. The composition as recited in claim 1, including by weight, 1 to 2000 parts of the n-acyl ethanolamine and 1 to 2000 parts of the at least one cannabinoid.

8. The composition as recited in claim 1, including by weight, 10 to 1800 parts of the n-acyl ethanolamine and 1 to 100 parts of the at least one cannabinoid.

9. A tablet comprising:
   one or more excipients;
   n-acyl ethanolamine;
   at least one cannabinoid; and
   at least one terpene, wherein the n-acyl ethanolamine is in the form of lyophilized, dry preassembled micelles, and the at least one cannabinoid is entrapped in the micelles.

10. The tablet as recited in claim 9, wherein the n-acyl ethanolamine is selected from the group consisting of olioylethanolamine, palmitoylethanolamide, and combinations thereof.

11. The tablet as recited in claim 9, wherein the at least one cannabinoid includes cannabigerolic acid.

12. The tablet as recited in claim 9, wherein the at least one terpene is selected from the group consisting of myrcene, limonene, caryophyllene, linalool, pinene, and combinations thereof.

13. The tablet as recited in claim 9, wherein the n-acyl ethanolamine is palmitoylethanolamide, the at least one cannabinoid includes cannabigerolic acid, and the at least one terpene includes myrcene.

14. The tablet as recited in claim 9, including by weight, 10 to 1800 parts of the n-acyl ethanolamine and 1 to 100 parts of the at least one cannabinoid.

15. A sublingual tablet comprising:
a compressed powder containing one or more excipients, n-acyl ethanolamine, at least one cannabinoid, at least one terpene, wherein the n-acyl ethanolamine is in the form of lyophilized, dry preassembled micelles, and the at least one cannabinoid is entrapped in the micelles.

16. The sublingual tablet as recited in claim 15, wherein the n-acyl-ethanolamine is selected from the group consisting of olioylethanolamide, palmitoylethanolamide, and combinations thereof.

17. The sublingual tablet as recited in claim 15, wherein the n-acyl-ethanolamine is palmitoylethanolamide, the at least one cannabinoid includes cannabigerolic acid, and the at least one terpene includes myrcene.

18. The sublingual tablet as recited in claim 15, wherein clinical activities associated with the administration of the sublingual tablet include: chronic and neuropathic pain, inflammation, including peripheral neuropathies such as diabetic neuropathy, chemotherapy induced peripheral neuropathy, carpal tunnel syndrome, phantom limb pain, sciatic pain, osteoarthritis, low back pain, musculo-skeletal pain, failed back surgery syndrome, fibromyalgia, dental pain, post-stroke neuropathic pain, pain from multiple sclerosis, chronic pelvic pain, intestinal inflammation, migraine, cerebral ischemia, complex regional pain syndrome, postherpetic neuralgia, chronic pain from Lyme's Disease, ALS, urinary pain, and vaginal pain.

* * * * *